United States Patent [19]

Falkowski et al.

[11] 4,136,161

[45] Jan. 23, 1979

[54] STABILIZED ERYTHROCYTES AND METHODS THEREFOR

[75] Inventors: Frank J. Falkowski, Lebanon; Leonard T. Wilson, Somerville, both of N.J.

[73] Assignee: Ortho Diagnostics, Inc., Raritan, N.J.

[21] Appl. No.: 667,316

[22] Filed: Mar. 16, 1976

[51] Int. Cl.$^2$ .................... A61K 35/18; A61K 39/00; G01N 33/16
[52] U.S. Cl. ........................................... 424/3; 424/8; 424/11; 424/12; 424/13; 424/75
[58] Field of Search ................... 424/3, 8, 11, 12, 13, 424/75

[56] References Cited

U.S. PATENT DOCUMENTS

| | | | |
|---|---|---|---|
| 3,548,051 | 12/1970 | Dingwall | 424/3 X |
| 3,553,310 | 1/1971 | Csizmas | 424/12 |
| 3,708,572 | 1/1973 | Peetoon | 424/3 X |
| 3,714,345 | 1/1973 | Hirata | 424/3 |
| 3,828,103 | 8/1974 | Fujita | 424/12 |
| 3,836,433 | 9/1974 | Wirth | 424/12 X |

OTHER PUBLICATIONS

Ling, Brit. J. of Haematol., vol. 7, 1961, pp. 299–302.
Emmel, Lab Tech in Biol. & Med., Robt. E. Krieger Pub. Co., Huntington, NY, 1970, Facsimile of 4th Ed., 1964, p. 183.

*Primary Examiner*—Anna P. Fagelson
*Attorney, Agent, or Firm*—Ralph T. Lilore

[57] ABSTRACT

A double aldehyde treatment process of erythrocytes is disclosed. Erythrocytes from various sources can be treated in a two-step process to render them stable and subsequently useful in antigen antibody detection systems. Glyoxal is used as a first treating medium followed by a second treatment step using formaldehyde or glyoxal as the fixative. Glyoxal is used in the first step in amounts ranging from 0.1 to 0.4 gm. per 0.8 ml. of Packed Cell Volume of erythrocytes, followed by the second treatment step in which at least 0.1 gm. of formaldehyde or glyoxal and preferably 0.1 to 0.6 gm. per 0.8 ml. Packed Cell Volume of treated erythrocytes is used. The reaction medium is preferably aqueous hypertonic and most preferably a sodium citrate medium. The treated cells can be used in detection of hepatitis associated antigen in a reverse passive hemagglutination test.

11 Claims, No Drawings

STABILIZED ERYTHROCYTES AND METHODS THEREFOR

This invention relates to the treatment of biological cell materials and more particularly to the treatment of erythrocytes. Specifically, it relates to the fixation of erythrocytes using a sequential two-stage coating technique involving certain aldehydic materials.

BACKGROUND OF THE INVENTION

In the field of medical diagnoses, it is very often convenient to use erythrocytes to aid in the detection of either antigens or antibodies in a test fluid. The erythrocyte in this case is used as a carrier particle for an attached antigen or antibody. As is known, when an antigenic material is brought into contact with an antibody which is specific for that material, an antigen-antibody reaction takes place. In some systems, this reaction is visibly perceptible, resulting in an antigen-antibody complex which can be discerned either by the naked eye or with the aid of laboratory visual equipment. In other cases, however, while there is an antigen-antibody reaction, the reaction product is not discernible either to the naked eye or with the aid of auxiliary equipment at any convenient level. In situations such as these, it is very useful to provide a particle medium as a vehicle for either the antigen or antibody so that subsequent reaction with the complexing partner can be visualized because clumping or agglutination of the particles is effected.

The art has used a variety of particulate materials as the base upon which to attach the antigen or antibody for subsequent reaction, including latex particles such as styrene, butadiene, acrylic polymers and various blood cells such as human and animal erythrocytes (red blood cells). Erythrocytes are a very fragile, delicate component of blood, constituting the basic medium upon which antigens are carried throughout the host system. For example, human red blood cells are known to carry a wide variety of various antigens, the nature and composition of which give rise to a fingerprint which is useful in determining what kind of blood a recipient could tolerate upon a transfusion.

When red cells are used to detect antigen-antibody reaction, the resulting agglutination is termed hemagglutination, and when the red cell is used to carry an antibody rather than an antigen for detection of a suspect antigen in host serum, the phenomenon is called reverse passive hemagglutination.

As illustration of a reverse passive hemagglutination is the well-known detection system for the presence of hepatitis associated antigen in a patient's serum. The difficulty with using red blood cells in such a hemagglutination system, or indeed in any antigen-antibody detection system, is that red cells are extremely fragile, delicate and unstable.

If red blood cells are left suspended in an isotonic medium, they will lyse within about twenty-one days. That is, the supporting structure of the red blood cells will start to weaken and cause the leakage of hemoglobin into the environment. Lysis of the cell results, making the material wholly unsuitable for any use in an agglutination detection system.

The present invention is concerned with treating red blood cells to improve their stability and permit their use in antigen-antibody reaction detection systems. The process of so treating red blood cells is called fixation.

THE PRIOR ART

Fixation of erythrocytes to improve stability is a well-known technique. Of course, in the selection of appropriate fixing agents, one has to be careful that the fixatives do not themselves contribute to lysis of the erythrocytes to any intolerable degree or have a substantial deleterious effect on the subsequent agglutination systems. While the phenomenon of cell protection is not fully understood, it is believed that the fixative causes a chemical reaction with protein components on the surface of the cell, resulting in a protected cell.

In U.S. Pat. No. 3,714,345, dated Jan. 30, 1973, the inventors describe a double aldehyde treatment process for coating erythrocytes using pyruvic aldehyde in a first treatment step followed by formaldehyde in a second step. This stabilization is stated by the patentee to be effective without apparent alteration of the capacity of the treated cells to react with anti-A or anti-B serum. That is, the patentee alleges that the stabilization is not effective to reduce this aspect of the antigenicity of red blood cells.

Other publications have indicated various techniques of fixation. For example, Ling in *Brit. J. Haemat.* (1961) 7; p. 299, shows the treatment of red blood cells with formaldehyde, pyruvic aldehyde, glyoxal, glutaric dialdehyde and glyoxylic acid. The author reports that pyruvic aldehyde is the preferred aldehyde for fixing red blood cells. The use of large amounts of glyoxal resulted in a treated cell which could not be consistently and reliably used as a base for attachment of serum proteins (such as antigens and antibodies). The author concluded that the glyoxal technique was unsuitable. Poor stability after six (6) months was obtained with glyoxal as opposed to the pyruvic aldehyde treated cells.

Red cells have also been treated with peroxy salt solutions (*Chem. Abstracts* [1961], p. 27495) and used in antigen-antibody agglutination systems (*Chem. Abstracts* [1961], p. 20672).

DETAILED DESCRIPTION OF THE INVENTION

In accordance with the present invention, it has now been discovered that erythrocytes can be stabilized in a two-step treatment involving contacting the cells with a quantity of glyoxal in a first treatment step followed by contacting the treated cells with a quantity of formaldehyde or glyoxal in a second treatment step. Glyoxal is an aldehyde which may exist in the monomeric, dimeric, trimeric or polymeric state. The monomer may be depicted structurally as

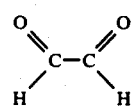

The material is a solid and is available commercially as the solid, dihydrated trimeric form having three moles of glyoxal and two moles of water per mole of trimer as follows:

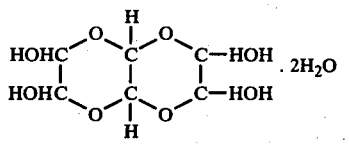

or as a 40% aqueous solution (based on the weight of monomeric free glyoxal). Formaldehyde is most often encountered as an aqueous solution of formaldehyde gas commercially available as formalin, 40% weight/volume (40 gms. formaldehyde per 100 ml. of aqueous solution).

The quantity of red blood cells in any volume of liquid whether the cells be from sheep, turkeys, rabbits, humans or any other animal, is conveniently referred to in terms of the volume that they occupy. A useful measure of the quantity of red blood cells in any liquid suspension of those cells is the volume of cells expressed as a percentage of the entire volume of the liquid suspension in a given sample. This parameter is termed Hematocrit or packed cell volume and gives a reliable representation of the red cells in terms of providing a common denominator for designating volumes. Hematocrit is a standardly determined parameter and is expressed as a percentage figure. Thus, a Hematocrit of 40% means that the red blood cells in 100 ml. of a liquid suspension of red blood cells occupy 40 ml. That is, the packed cell volume is 40 ml. It can be seen, therefore, that if the volume of the liquid suspension is doubled while the volume of the red cells in that suspension remains the same, the Hematocrit will be one-half the original, i.e. 20% in the case of the example given above.

Hematocrit is determined conventionally by using the standard laboratory macromethod of Wintrobe, as described in *Clinical Diagnosis By Laboratory Methods*, 14th Edition, W. B. Saunders Company (Publishers), Edited by Israel Davidsohn, M.D., F.A.C.P., and John Bernard Henry, M.D. At page 146 of that reference book, the macromethod is described as follows:

"EQUIPMENT. The Wintrobe Hematocrit tube is a thick-walled glass tube with a uniform internal bore and a flattened bottom. It is graduated in millimeters from 0 to 105 and has a rubber cap to prevent evaporation during the long period of centrifugation.

Of the various forms of filling pipettes available, a 2-ml. syringe with a needle long enough to reach the bottom of the hematocrit tube is probably as good as any and quite practical.

The essential requirement of a centrifuge is that it generate a centrifugal field of not less than 2500 G. at the bottom of the cup."

"REAGENT. For an anticoagulant, dried heparin, balanced oxalate or EDTA is satisfactory. If an inadequate amount of blood is drawn into the tube, resulting in an excess of oxalate or EDTA, the erythrocytes will shrink and the hematocrit will be falsly low."

"PROCEDURE. The oxalated or heparinized blood must be mixed thorougly by not less than 30 slow and complete inversions of the container. Rolling the bottle in inadequate, and shaking is still worse because it may damage the cells."

"After adequate mixing, the hematocrit tube is filled using the filling pipette or a syringe, preferably in one operation. The tip of the pipette is introduced to the bottom of the tube. As filling proceeds, the tip of the pipette is raised, but it remains under the rising blood meniscus in order to avoid foaming. The level of the blood should be noted and the tubes capped to avoid evaporation during the required centrifugation for 30 minutes at 2500 G."

"Reading is done without disturbing the specimen. The result is calculated from the formula:

Hematocrit (percent) = $100 L_1/L_2$ where $L_1$ is the height of the red cell column in mm. and $L_2$ is the height of the whole blood specimen (red cells and plasma). The gray-white layer of leukocytes and platelets above the erythrocytes is not included in $L_1$."

It has been found in accordance with the present invention that the amount of glyoxal and formaldehyde used in the treatment steps can be conveniently related to a unit of Hematocrit measurement using the technique described above. A Hematocrit value will tell one skilled in the art what the red cell packed volume is. This volume will not ordinarily change from sample to sample of blood to any significant degree as regards the present invention provided the conditions for centrifuging samples are substantially equivalent. Thus a Hematocrit obtained on, for example, sheep erythrocytes can be compared to a Hematocrit obtained on turkey erythrocytes or human erythrocytes as regards the determination of the amount of fixative to be used in practicing the present invention. As used herein, Hematocrit value signifies the packed cell volume of red cells using the macromethod of Wintrobe at a force of at least 2500 G. for 20–30 minutes. Additionally, the term "Packed Cell Volume" when used herein means that volume of red cells obtained under the foregoing conditions, unless otherwise stated in the text.

A convenient Hematocrit value for practicing the present invention is 8%. This corresponds to 0.8 ml. of Packed Cell Volume per 10 ml. of liquid red cell suspension. This concentration gives a conveniently handled liquid suspension of red cells which is far less viscous than whole blood yet concentrated enough to treat significant amounts of cells. In accordance with the present invention, the amount of glyoxal used in the first treatment step is within the range of 0.1 to 0.4 gms. and preferably 0.1 to 0.3 gms. glyoxal per 0.8 ml. of Packed Cell Volume. It is most convenient to supply the appropriate amount of glyoxal in the form of a dilute solution thereof, of the order of 1 to 4% (1–4 gm. glyoxal [based on the free monomer] dissolved per 100 ml. solution). This is suitably obtained by diluting commercially available 40% glyoxal to the appropriate concentration.

In carrying out the process of the present invention, red blood cells are selected depending to a large extent on the subsequent antigen-antibody reaction that they will be employed to detect. In many situations, human cells are desired, but of equal suitability are the erythrocytes of sheep, horses, chickens, turkeys and rabbits. The contacting of the erythrocytes by the glyoxal is conducted in the presence of an aqueous medium, which has a degree of tonicity substantially compatible with the integrity of the cells, preferably a hypertonic medium, such as sodium citrate solution, for periods ranging preferably from 18-24 hours. Shorter and longer periods do not usually result in added benefit. The temperature of reaction is usually 18°–25° C. with room temperature being preferred.

The actual concentration of sodium citrate in the final medium will depend upon several factors including the dilutions of the aldehyde, the particular erythrocytes used and the like. Suitably, the aqueous medium comprises sodium citrate (based on the dihydrate) in the range of 4.5 to 5% weight/volume.

The first treatment step of the invention is a critical event in the stabilization of the erythrocytes. The very delicate, fragile, untreated erythrocytes are converted in this step to a more stable form, capable of tolerating variations of environment and conditions that the untreated cell could not. In view of this result, the conditions of the second treatment step may vary more widely and more drastically than those of the first treatment step as will be seen below.

Following treatment in the first stage, the cells are washed free of any hemolysed cells that may have resulted, usually with an isotonic saline solution, and then treated in the second step with either formaldehyde or glyoxal at levels of at least 0.1 and preferably ranging from 0.1 to 0.6 gm. and most preferably 0.1–0.3 gm. per 0.8 ml. of Packed Cell Volume. This treatment is conveniently carried out under the same conditions as the first glyoxal treatment although concentrations of the second aldehyde at the high end of the ranges tend to require shorter treatment times. After the second treatment is completed, the cells are then washed using preferably a saline or a buffer wash medium and are then ready for coating with antigen or antibody for subsequent use in a detection system.

Cells treated in accordance with the present invention have been stable at 5° C. for over eight months, have not shown any signs of hemolysis and are suitable for coating with antigen or antibody. This is to be contrasted to the situation obtained with untreated cells wherein hemolysis begins almost immediately and is usually complete in about twenty-one days.

Additionally, the treated cells retain their ability to be coated with antibody or antigen and react specifically. For example, antibody or antigen can be attached to the treated cell in accordance with well-known techniques. Various antigens and antibodies such as Human Chorionic Gonadatropin, hepatitis antibody, fibrinogen, albumin, gammaglobulin and the like may be used.

The conditions set forth above for determining Hematocrit were presented to (a) give a standard for all sources of red cells; and
(b) to utilize the most commonly encountered laboratory procedures. If different determination conditions are employed or if electronic cell counters are used, resulting in a red cell packed volume different from that obtained utilizing the Wintrobe conditions referred to previously, one should relate that red cell packed volume to a Hematocrit obtained at the prescribed Wintrobe conditions for calculation of the amount of fixatives to be used herein.

The buffers or diluents used herein may be any of the biologically suitable materials normally used in the art, which are substantially compatible with the integrity of the cells. The term "biologically suitable" includes compatibility with the antigens or antibodies encountered and with non-lysis of erythrocytes. Such materials as solutions of normal saline, sodium citrate and the like may be used. Sodium citrate solutions of about 4.5–5% weight/volume are most preferred.

EXAMPLE I 100 ml. of type O Rh negative blood was collected from a human donor in a standard acid-citrate-dextrose (ACD) anticoagulant medium. The cells were washed four times in 10 volumes of iostonic saline. The cells were resuspended in one of two buffers as indicated below at a level of 8% Hematocrit (using the Wintrobe macromethod). The buffers had the following composition:

1. Citrate — 5.0% weight volume aqueous sodium citrate . $2H_2O$, having a pH of 8.7; and
2. Phosphate — 16.18 gm. $Na_2HPO_4$-anhyd 4.9 gm. $KH_2PO_4$ - anhyd pH 7.2 (0.15M)

Various dilutions of 40 g. % aqueous glyoxal (based on free monomer) were prepared as indicated in the table below using the buffer indicated. 10 ml. of the buffered glyoxal solution were then mixed with 10 ml. of cell suspension. Thus, in each case, 0.8 ml. of red cell packed volume was contacted by the indicated amount of glyoxal.

| | % Glyoxal | gms. Glyoxal | Ald. Buffer | Cell Buffer |
|---|---|---|---|---|
| A | 4 | 0.4 | Citrate | Citrate |
| B | 4 | 0.4 | Citrate | Citrate |
| C | 4 | 0.4 | Citrate | Citrate |
| D | 4 | 0.4 | Citrate | Citrate |
| E | 6 | 0.6 | Citrate | Citrate |
| F | 1 | 0.1 | Phosphate | Phosphate |
| G | 3 | 0.3 | Phosphate | Phosphate |
| H | 5 | 0.5 | Phosphate | Phosphate |

Each sample was mixed on a magnetic stirrer at 20°–25° C. for 18–24 hours. The fixed cells in each sample were then separately washed 4 times in saline, then readjusted to 8% Hematocrit in the 5% citrate buffer described above.

EXAMPLE II

The indicated volumes of each of the samples A through H obtained in Example I were treated with the aldehyde shown below in the amounts indicated.

| Sample | Vol. of Treated Cell Suspension | Treated Red Cell Suspension Buffer | Aldehyde | Volume | Aldehyde Buffer | Aldehyde % | Weight of Aldehyde Present |
|---|---|---|---|---|---|---|---|
| $A_G$* | 10 ml. | Citrate | Form.[1] | 10 ml. | Citrate | 1.1% | 0.11 g. |
| $B_G$ | 10 ml. | Citrate | Form. | 10 ml. | Citrate | 5.4% | 0.54 g. |
| $C_G$ | 10 ml. | Citrate | Glyoxal[2] | 10 ml. | Citrate | 1.0% | 0.1 g. |
| $D_G$ | 10 ml. | Citrate | Glyoxal | 10 ml. | Citrate | 5.0% | 0.5 g. |
| $E_G$ | 1.15 ml. | Citrate | Form. | 1.15 ml. | Citrate | 3.2% | 0.037 g. |
| $F_G$ | 6.3 ml. | Citrate | Form. | 6.3 ml. | Citrate | 3.2% | 0.2 g. |
| $G_G$ | 10 ml. | Citrate | Form. | 10 ml. | Citrate | 3.2% | 0.32 g. |
| $H_G$ | 10 ml. | Citrate | Form. | 10 ml. | Citrate | 3.2% | 0.32 g. |

*In each case G means glyoxal treated.
[1] 40% w/v formaldehyde solution diluted to indicated aldehyde % with citrate buffer.
[2] 40% w/v glyoxal solution diluted to indicated aldehyde % with citrate buffer.

The cells were mixed with the aldehyde at room temperature for 18–24 hours. They were then washed four times in saline, adjusted to 8% Hematocrit in 0.1 M phosphate buffer having the following composition:

3.26 gm. KH$_2$PO$_4$ (anhydrous)
10.78 gm. Na$_2$HPO$_4$ (anhydrous)
1 gm. NaN$_3$
q.s. to 1 liter The cells were permitted to sit at +5° C. for one week and then were inspected for hemolysis. The supernatant of samples F, G and H was yellow, indicating that the cells were not fully stabilized.

EXAMPLE III

Each of the samples A through H obtained in Example II was utilized in an antigen-antibody detection system as follows:

One hundred twenty-five (125) μl. of the 8% Hematocrit cells suspension in the 0.1 M phosphate buffer are dispensed into a test tube. The cells are washed once with isotonic saline, the saline decanted and 0.5 ml. of 0.1 M acetate buffer[1], pH 4 is added to the cells. To this is added 5-20 micrograms of affinity purified hepatitis B$_s$ antibody from a chimpanzee, and the suspension mixed at room temperature for 75 minutes. The cells are then washed 4 times with isotonic saline, the saline decanted and cells suspended in 0.1 M phosphate buffer described in Example II and additionally containing 0.01 M EDTA, 1% normal human serum, and 0.1% gelatin. A 25 μl. sample of each cell suspension was then introduced into a microtitre well containing 25 μl. of a diluent and 7 μl. of either (a) human serum known to contain hepatitis B antigen (weakly positive by radioimmunoassay technique);

(b) human serum known to be negative for hepatitis B antigen by radioimmunoassay techniques;

(c) nothing in addition to the diluent (the control well).

[1]2.45 gms. NaC$_2$H$_3$O$_2$. 3H$_2$O
4.7 ml. acetic acid (glacial)
q.s. to 1,000 ml. with distilled water In each case, the antibody coated cells were mixed by shaking and allowed to stand undisturbed for 2 hours at room temperature. The wells were thereafter examined for the presence of an agglutination reaction. Examples A through D gave reactions for the positive serum and no reaction with the known negatives. The control gave no reaction.

Sample E was prepared by using the 0.6 gm. glyoxal/0.8 ml. Packed Cell Volume, and gave non-specific reactions with negatives.

Samples F through H were found not to react specifically indicating that they were unsuitable for use in a hepatitis B$_s$ antigen detection system.

Summarizing the previous examples, the following shows the amounts of glyoxal and formaldehyde or glyoxal on the treated cells, Gx. indicating glyoxal, F. is formaldehyde, and the numbers preceding each signify the grams in tenths, per 0.8 ml. of Packed Cell Volume.

| | | | |
|---|---|---|---|
| A | 4 Gx. 1 F. | - | Specific Reaction |
| B | 4 Gx. 5 F. | - | Specific Reaction |
| C | 4 Gx. 1 Gx. | - | Specific Reaction |
| D | 4 Gx. 5 Gx. | - | Specific Reaction |
| E | 6 Gx. 3 F. | - | Non-Specific Reaction |
| F | 1 Gx. 3 F. | - | Non-Specific Reaction |
| G | 3 Gx. 3 F. | - | Non-Specific Reaction |

-continued

| | | | |
|---|---|---|---|
| H | 5 Gx. 3 F. | - | Non-Specific Reaction |

EXAMPLE IV

Example I was repeated to produce appropriately treated red blood cells using the following amounts of materials in the first treatment step.

| Glyoxal Treatment in Citrate Buffer - Red Cells in Citrate | | |
|---|---|---|
| Sample | % Aldehyde | Gms. Aldehyde |
| 1 | 1 (Glyoxal) | .1 |
| 2 | 1 (Glyoxal) | .1 |
| 3 | 1 (Glyoxal) | .1 |
| 4 | 1 (Glyoxal) | .1 |
| 5 | 5 (Glyoxal) | .5 |
| 6 | 5 (Glyoxal) | .5 |
| 7 | 5 (Glyoxal) | .5 |
| 8 | 5 (Glyoxal) | .5 |
| 9 | 3 (Glyoxal) | .3 |
| 10 | 3 (Glyoxal) | .3 |
| 11 | 3.2 (Formaldehyde) | .32 |
| 12 | 3.2 (Formaldehyde) | .32 |

The second fixing stage was carried out following the procedure of Example II using the aldehyde indicated below:

| Sample | % Aldehyde | Gms. Aldehyde/ .8 ml. Packed Cell Vol. |
|---|---|---|
| 1 = 1 Gx. | 1.1 Form. | 0.11 |
| 2 = 1 Gx. | 5.4 Form. | 0.54 |
| 3 = 1 Gx. | 1 Gx. | 0.1 |
| 4 = 1 Gx. | 5 Gx. | 0.5 |
| 5 = 5 Gx. | 1.1 Form. | 0.11 |
| 6 = 5 Gx. | 5.4 Form. | 0.54 |
| 7 = 5 Gx. | 1 Gx. | 0.1 |
| 8 = 5 Gx. | 5 Gx. | 0.5 |
| 9 = 3 Gx. | 3 Gx. | 0.3 |
| 10 = 3 Gx. | 3.2 Form. | 0.32 |
| 11 = 3.2 Form. | 3.2 Form. | 0.32 |
| 12 = 3.2 Form. | 3 Gx. | 0.3 |

Samples 1–4 and 9 and 10 showed specific reactions for HB$_s$Ag following the procedure set forth in Example III and gave no reactions for controls and known negatives.

Samples 5–8 give non-specific reactions for HB$_s$Ag in the negative samples.

Samples 11 and 12 give no specific reaction for positive HB$_s$Ag and are therefore unsuitable.

What is claimed is:

1. The method for stabilizing erythrocytes which comprises contacting erythrocytes in biologically suitable aqueous medium in a first treatment step with from 0.1 to 0.4 gms. of glyoxal per 0.8 ml. of Packed Cell Volume of said erythrocytes to obtain treated erythrocytes, and thereafter contacting said treated erythrocytes in biologically suitable aqueous medium in a second treatment step with at least 0.1 gms. of formaldehyde or glyoxal per 0.8 ml. of Packed Cell Volume of said treated erythrocytes, said aqueous medium being hypertonic and having a degree of tonicity substantially compatible with the integrity of the erythrocytes.

2. The method of claim 1 wherein the aqueous medium of said first and second treatment steps comprises a hypertonic sodium citrate solution.

3. The method of claim 2 wherein the first treatment step is conducted for 18–24 hours at temperatures of from 18°–25° C.

4. The method of claim 3 wherein the second step is conducted for 18-24 hours at temperatures of from 18°-25° C.

5. The method of claim 2 wherein the erythrocytes are treated in step 2 with from 0.1 to 0.6 gms. of formaldehyde or glyoxal.

6. The method of claim 5 wherein the treated erythrocytes from the first treatment step are separated from the aqueous medium and washed before treatment in the second treatment step.

7. The method for preparing stabilized erythrocytes useful in the passive hemagglutination detection of hepatitis associated antigen which comprises contacting
   (1) a hypertonic aqueous suspension comprising human erythrocytes and 4.5-5% weight/volume of sodium citrate, with
   (2) a quantity of an aqueous solution of glyoxal comprising 4.5-5% weight/volume of sodium citrate, said quantity being sufficient to supply from 0.1-0.4 gms. of glyoxal per 0.8 ml. of Packed Cell Volume of said erythrocytes;
   (3) separating said glyoxal treated cells from said suspension;
   (4) forming a second hypertonic aqueous suspension comprising said treated erythrocytes and 4.5-5% weight/volume of sodium citrate; and
   (5) contacting said second hypertonic aqueous suspension of erythrocytes with a quantity of an aqueous solution of glyoxal or formaldehyde comprising 4.5-5% weight/volume of sodium citrate, said quantity being sufficient to supply 0.1-0.6 gms. of glyoxal or formaldehyde per 0.8 ml. of Packed Cell Volume of said treated erythrocytes.

8. The method of claim 7 wherein the first and second treatment steps are conducted at 18°-25° C.

9. The method of claim 8 wherein the first and second treatment steps are carried out for 18-24 hours.

10. Indicator erythrocytes useful in antigen-antibody detection which comprises erythrocytes chemically reacted in an aqueous medium with from 0.1 to 0.4 grams of glyoxal per 0.8 ml. of packed volume of said erythrocytes and then in an aqueous medium with at least 0.1 grams of formaldehyde per 0.8 ml. of Packed Cell Volume of glyoxal reacted erythrocytes, said aqueous medium being substantially compatible with the integrity of the erythrocytes.

11. The indicator erythrocytes of claim 10 wherein the formaldehyde is employed at a level of 0.1 to 0.6 grams of formaldehyde per 0.8 ml. Packed Cell Volume of glyoxal reacted erythrocytes.

* * * * *